United States Patent
Farin et al.

(10) Patent No.: US 6,348,051 B1
(45) Date of Patent: Feb. 19, 2002

(54) PREPARATION INSTRUMENTS

(75) Inventors: Günter Farin, Tübingen; Klaus Fischer, Nagold, both of (DE)

(73) Assignee: Erbe Elektromedizin GmbH, Tubingen (DE)

( * ) Notice: Subject to any disclaimer, the term of this patent is extended or adjusted under 35 U.S.C. 154(b) by 0 days.

(21) Appl. No.: 09/462,949

(22) PCT Filed: Jul. 14, 1998

(86) PCT No.: PCT/EP98/04386

§ 371 Date: Mar. 20, 2000

§ 102(e) Date: Mar. 20, 2000

(87) PCT Pub. No.: WO99/03406

PCT Pub. Date: Jan. 28, 1999

(30) Foreign Application Priority Data

Jul. 14, 1997 (DE) .......................... 197 30 127

(51) Int. Cl.⁷ ................................ A61B 18/18
(52) U.S. Cl. ............... 606/49; 606/45; 606/37
(58) Field of Search ............... 606/41–50, 32, 606/34, 36, 37

(56) References Cited

U.S. PATENT DOCUMENTS

| 4,781,175 A | 11/1988 | McGreevy et al. |
| 5,256,138 A | * 10/1993 | Burek et al. .................... 606/45 |
| 5,449,356 A | 9/1995 | Walbrink et al. |
| 5,669,907 A | * 9/1997 | Platt, Jr. et al. ............... 606/48 |
| 5,766,169 A | * 6/1998 | Fritzsch et al. ............... 606/48 |
| 5,776,092 A | 7/1998 | Farin et al. |

FOREIGN PATENT DOCUMENTS

| DE | 4139029 A1 | 5/1993 |
| DE | 9409884 U1 | 11/1995 |
| EP | 0688536 A1 | 12/1995 |
| WO | WO 92/05743 | 4/1992 |
| WO | WO 93/01758 | 2/1993 |

\* cited by examiner

Primary Examiner—Linda C. M. Dvorak
Assistant Examiner—David Ruddy
(74) Attorney, Agent, or Firm—Marshall, Gerstein, & Borun

(57) ABSTRACT

In a dissecting instrument for surgical operations a working instrument such as a blade with cutting edge is fastened to a holding device such as a handle. Coagulation devices are provided, with a gas-supply apparatus to supply an ionizable (noble) gas and current-conducting means to supply an HF coagulation current. It is proposed to mount electrode devices that form part of the current-conducting means in such a way that they are separate from the working instrument but nevertheless close to it, and to make the working instrument electrically insulating so that the coagulation current can be guided to the tissue without being conducted through the working instrument even while the latter is in contact with the tissue.

14 Claims, 7 Drawing Sheets

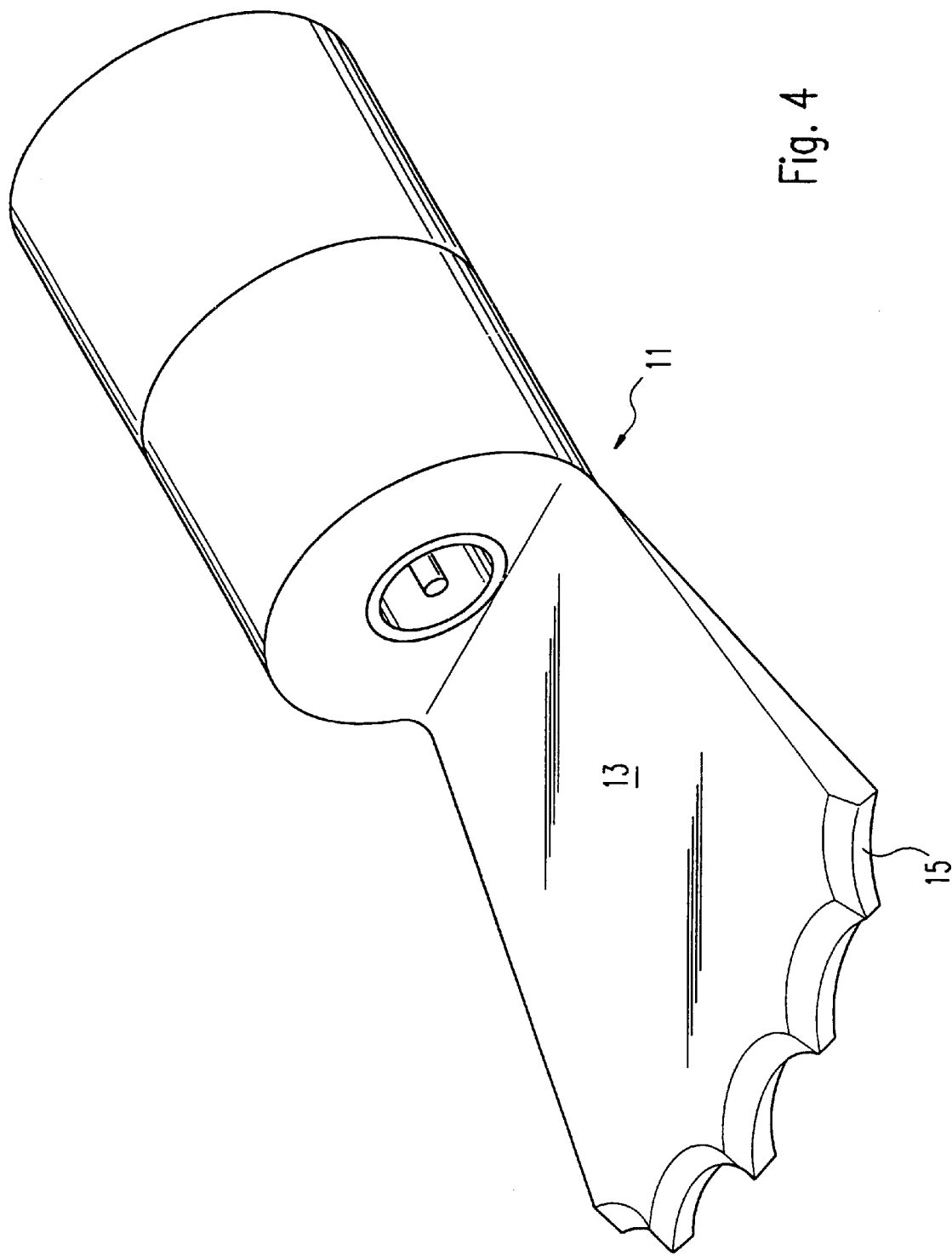

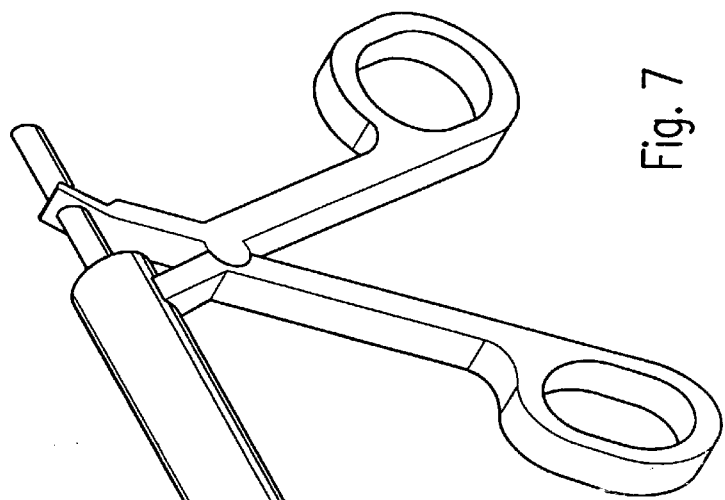
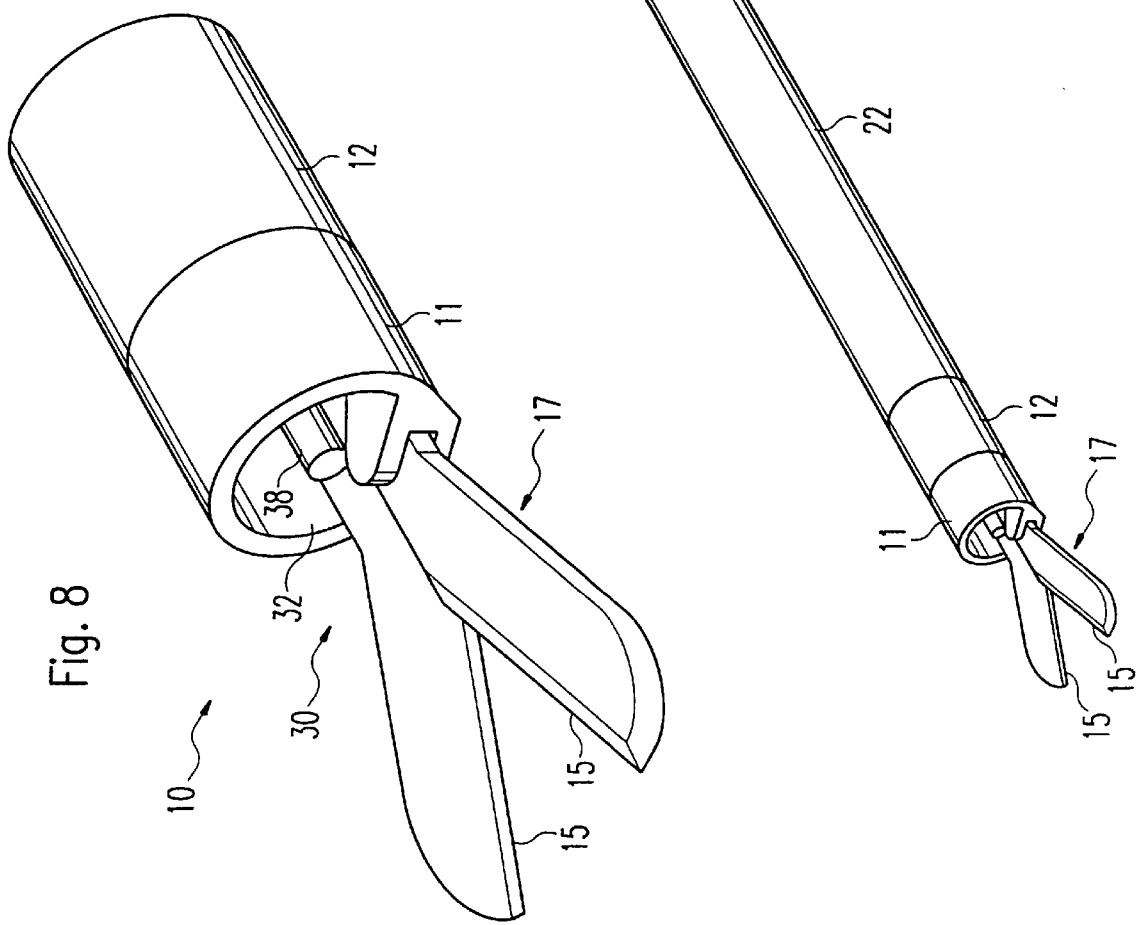

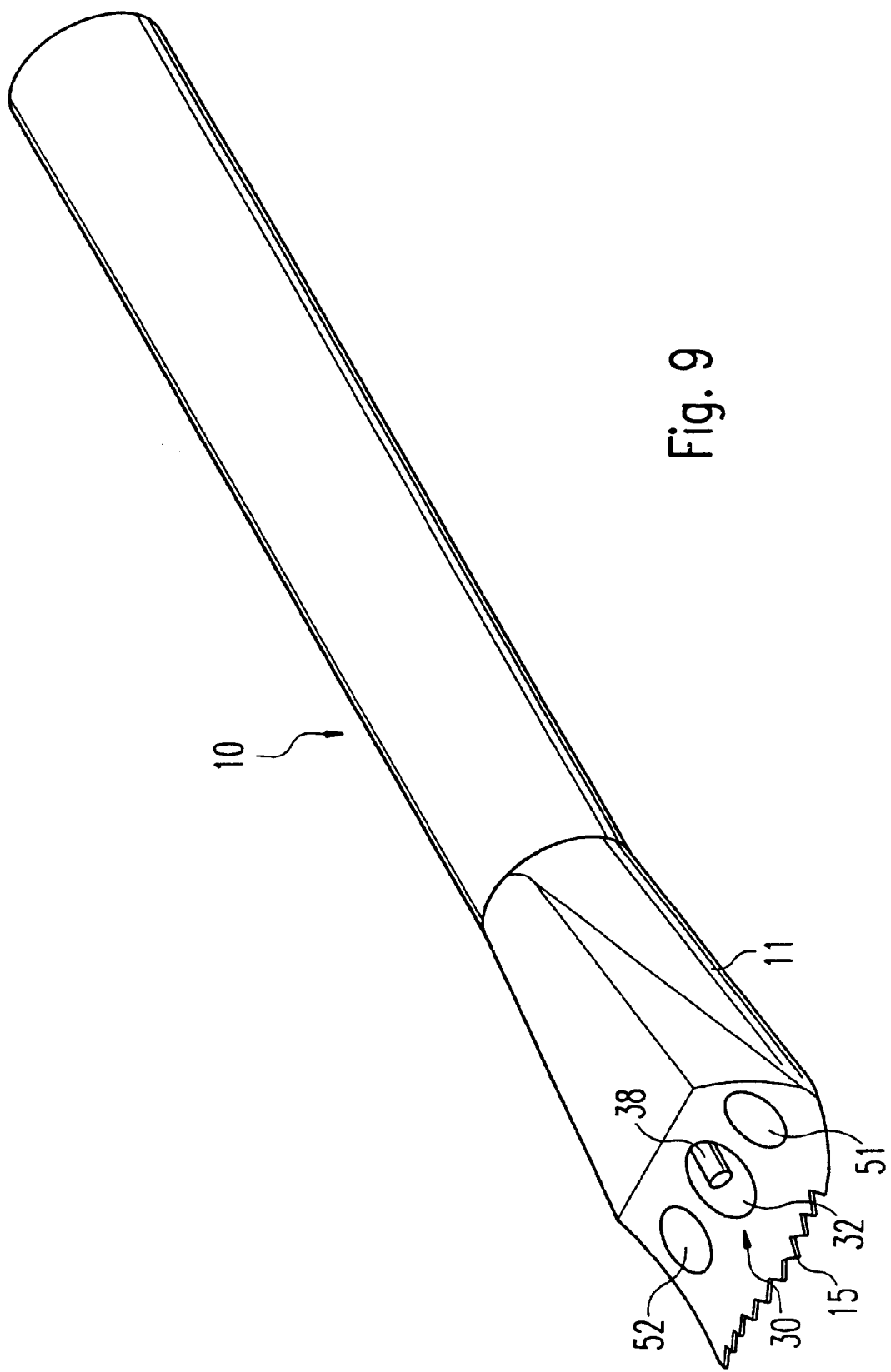

PREPARATION INSTRUMENTS

The invention relates to a dissection instrument for surgical operations.

BACKGROUND OF THE INVENTION

During surgical operations, cuts made in the tissue cause blood vessels to become injured. The emerging blood impairs visibility for the surgeon, and it is also important to minimize loss of blood by the patient. A typical example of an operation that frequently involves severe bleeding is tonsillectomy.

To stanch bleeding, the patents DE 41 39 029 A1 or DE 37 10 489 A1 disclose coagulation devices with which a high-frequency current is caused to flow through a noble-gas atmosphere between an electrode and the tissue, by ionizing the noble gas and thus producing a plasma. As a result of the heat thereby generated, the tissue is coagulated. Such a device must be used in addition to the dissection instrument.

The patent WO 93/01758 discloses a coagulation device in which a dissection instrument, a needle, scissors, loop or the like is movably disposed in a conduit for the noble gas, so that the operator can move the arrangement after it has been placed within an endoscope. In this case the dissection instrument is employed either entirely mechanically, e.g. as a cutting tool, or as an electrosurgical instrument by production of a direct flow of current between the instrument and the tissue. Furthermore, in this known arrangement the surgical instrument can be used as electrode to generate a plasma, as is likewise the case for the objects of the documents cited above. The manipulation of the known instrument during coagulation is very critical, because it is absolutely necessary to avoid contact between the instrument, while in use as an electrode, and the tissue, so that the latter is not locally destroyed. In addition care must be taken not to switch the coagulation current on accidentally during the dissection, because then the current would act on the tissue by direct conduction through the instrument. Elaborate measures must be taken to ensure this temporal separation of the two functions.

The object of the invention is to disclose a simple dissection instrument for surgical operations that is extremely user-friendly while functioning in an improved manner.

SUMMARY OF THE INVENTION

It is an essential point of the invention that the disclosed arrangement enables substantially simultaneous dissection and coagulation with one and the same instrument. Thus it is possible practically during the cutting to stanch the bleeding that is caused, or to close tissue, with no increased manual effort. As a result, the duration of the operation is considerably decreased, blood losses and hence the disadvantages cited above are diminished or even prevented, and nevertheless the demands made on the operator are reduced.

Preferably the working instrument as a whole is made of a plastic, a ceramic or a similarly insulating material, which is relatively simple with regard to manufacturing technology. Alternatively, or where appropriate additionally in certain sections, the working instrument can be coated with a plastic or ceramic material or the like, so that there is no possibility of a flow along the instrument to the tissue of an electrical current that might interfere with the flow of the coagulation current from electrode to tissue.

An important aspect here is the fact that during plasma coagulation it happens automatically, so to speak, that the "admission" of a current is possible only into those parts of the tissue that have a sufficiently high conductance. This sufficiently high conductance is simultaneously also a measure of how "open" or moist the tissue is at its surface. As soon as an adequately large coagulation effect has been achieved, so that the surface of the tissue is "dry", the coagulation current seeks another path or is interrupted, if the controllable HF source is appropriately (with respect to voltage and/or current) adjusted. The insulated working instrument can thus not disturb this "self-regulation". Preferably the electrode device, which comprises an electrode holder and an electrode, in particular a wire electrode, is disposed close to the working instrument and preferably is fixed thereto. This enables a simple and nevertheless particularly compact construction, so that the coagulation current can flow very directly to the tissue sections in which the working instrument is making changes at that moment.

The gas-supply apparatus comprises an outflow opening of a gas conduit that is disposed close to the working instrument, next to or surrounding the electrode device. This feature, again, leads to an especially simple and compact construction.

The dissection instrument can be made particularly simple, stable and small if the working equipment and the electrode holder are constructed substantially in one piece. In this case, the gas outlet is preferably also integrated into the working equipment.

It is further advantageous for the working equipment and at least a distal end section of the holding device to be constructed substantially in one piece.

The electrode device is preferably constructed and disposed in such a way that direct electrical contact between the electrode device and the tissue is prevented. This can be achieved, for example, in the case of an electrode disposed in the gas outlet by positioning the electrode some distance behind the opening. It is also possible to surround the electrode itself with a protective cage or the like, to prevent direct contact with the tissue.

The stream of noble gas should be "soft" enough that it has no mechanical effect and also that only a very small amount of gas is consumed, as the presence of large amounts of gas would be highly disadvantageous in various sites of application. In order nevertheless to be able to remove liquid, tissue fragments or other solids from the tissue surface with no supplementary instruments, in particular to expose the operation field and achieve a better coagulating action, it is possible to provide in addition (where appropriate, also made integral with the devices described previously) equipment such as suction, blowing or rinsing devices. For instance, in addition to the gas conduit for supplying ionizable (noble) gas to produce the coagulation current, a gas nozzle can be provided to blow liquid away. A simultaneous extraction by suction, for instance through an additional channel, is likewise possible. It will be self-evident that several channels can serve various functions in alternation, such as a rinsing and a suction function.

Furthermore, it is possible to provide additional supplementary electrosurgical instruments, such as an electrode in a needle, spherical or flat configuration, or else a wire loop, in order to perform special functions (e.g., polypectomy).

Preferably the holding device is exchangeable, with simultaneous coupling and decoupling of the gas and current supplies, so that while the coagulation conditions are maintained (with respect to gas and current flow) the working instrument can be changed.

To ensure coagulation conditions as nearly optimal as possible, it is advantageous for cleaning means to be provided to keep the electrode device free of liquid or similar substances that could make it dirty or alter the current flow. In particular when the electrode device is disposed within the gas outlet, the electrode can be kept free by ensuring that a substantially continuous (very slight) gas stream flows around the electrode device.

BRIEF DESCRIPTION OF THE DRAWINGS

In the following the invention is explained with reference to drawings of exemplary embodiments, wherein FIGS. 2 to 4 show different variants of working-instrument heads, FIG. 7 is a perspective view of another embodiment of a working instrument, FIG. 8 shows a detail of the end region of the instrument according to FIG. 7 and FIG. 9 is a perspective view of another working instrument.

DETAILED DESCRIPTION

Figure 1:
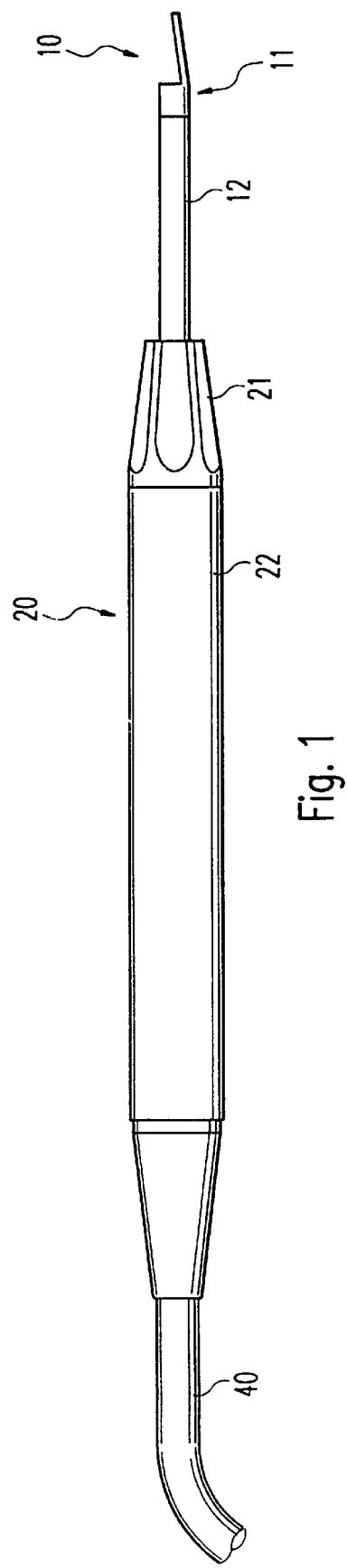
FIG. 1 shows an embodiment of the invention from the side.

In the following description, the same reference numerals are used for identical parts or parts with identical actions.

In FIG. 1 an embodiment of a dissection instrument for surgical operations is shown in side view; it comprises at its front end a working instrument 10 that is fixed by way of a shaft 12 within an attachment cone 21 of a handle 22 of a holding device 20. Into a back end of the holding device 20 a connecting tube 40 is inserted.

The working instrument 10 comprises, attached to the shaft 12, a head 11 various embodiments of which will be described in the following.

Figure 2:
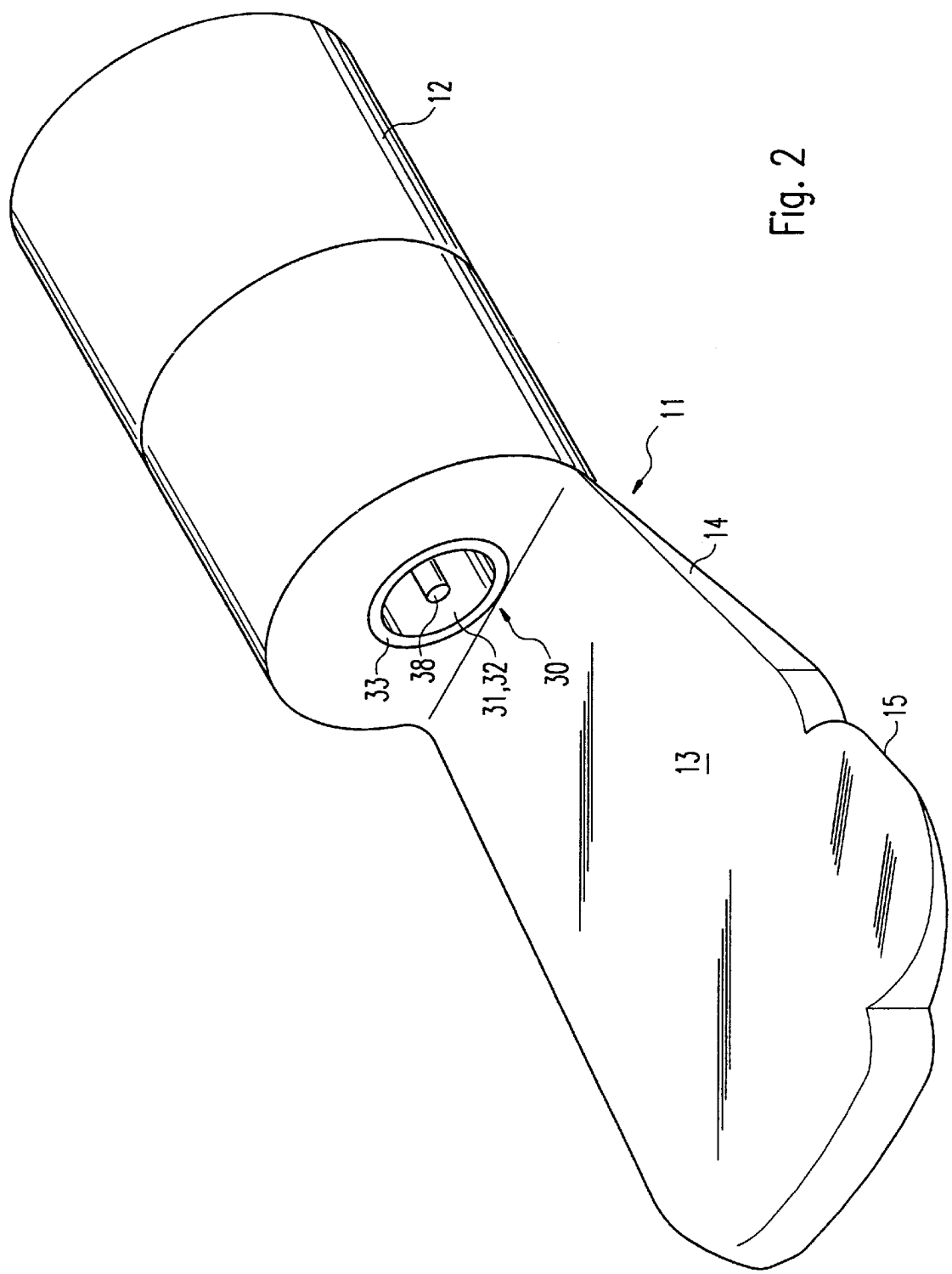

The embodiment of the head 11 shown in FIG. 2 is a scalpel-like instrument with a surface 13, the margin 14 of which is provided with a cutting edge 15.

In the head 11 is further provided a coagulation device 30, which comprises an outlet 32 of a gas-supply apparatus 31 that is combined with to a gas conduit 33 through which an ionizable gas, in particular a noble gas, preferably argon or helium, is conducted.

In the interior of the outlet 32, preferably so disposed as to prevent contact with tissue, there is an electrode 38, which is connected to a current conductor (not shown). To this electrode 38 there can be supplied a high-frequency coagulation current, the magnitude or voltage of which can be adjusted or regulated in a manner known per se.

The head 11 of the working instrument 10 shown here, and of course also the gas conduit 33, are made of an electrically non-conducting material or are coated with such a material, so that a coagulation current passing through the electrode 38 is not disturbed by the head 11 but can flow exclusively—through the plasma that forms in a known manner—to the tissue next to the head 11 of the working instrument.

Now when the operator, while or immediately after guiding the cutting edge 15 into or through tissue, turns the coagulation current on, preferably by means of a foot switch or a switch mounted on the handle 22, a plasma discharge forms and the coagulation current flows into the tissue. In this process a kind of self-regulation can be discerned, in that the coagulation current primarily enters the tissue where it has just been cut and hence is particularly moist. The same applies of course to blood vessels, which—when just opened—present an especially low electrical "surface resistance", so that the coagulation effect is particularly strong. As the process of coagulation or of tissue drying proceeds, the resistance at this site rises, so that the discharge "seeks" another site or, if the HF current supply is appropriately adjusted, ceases because of the resistance then encountered. The substantial advantage to the operator here is thus that essentially during the cutting process, or at least very soon thereafter, coagulation can occur immediately so that bleeding is reduced to a minimum. This in turn facilitates the operator's work and protects the patient. This applies especially, for instance, to tonsillectomy, in which bleeding is well known to constitute a serious problem.

Figure 3:
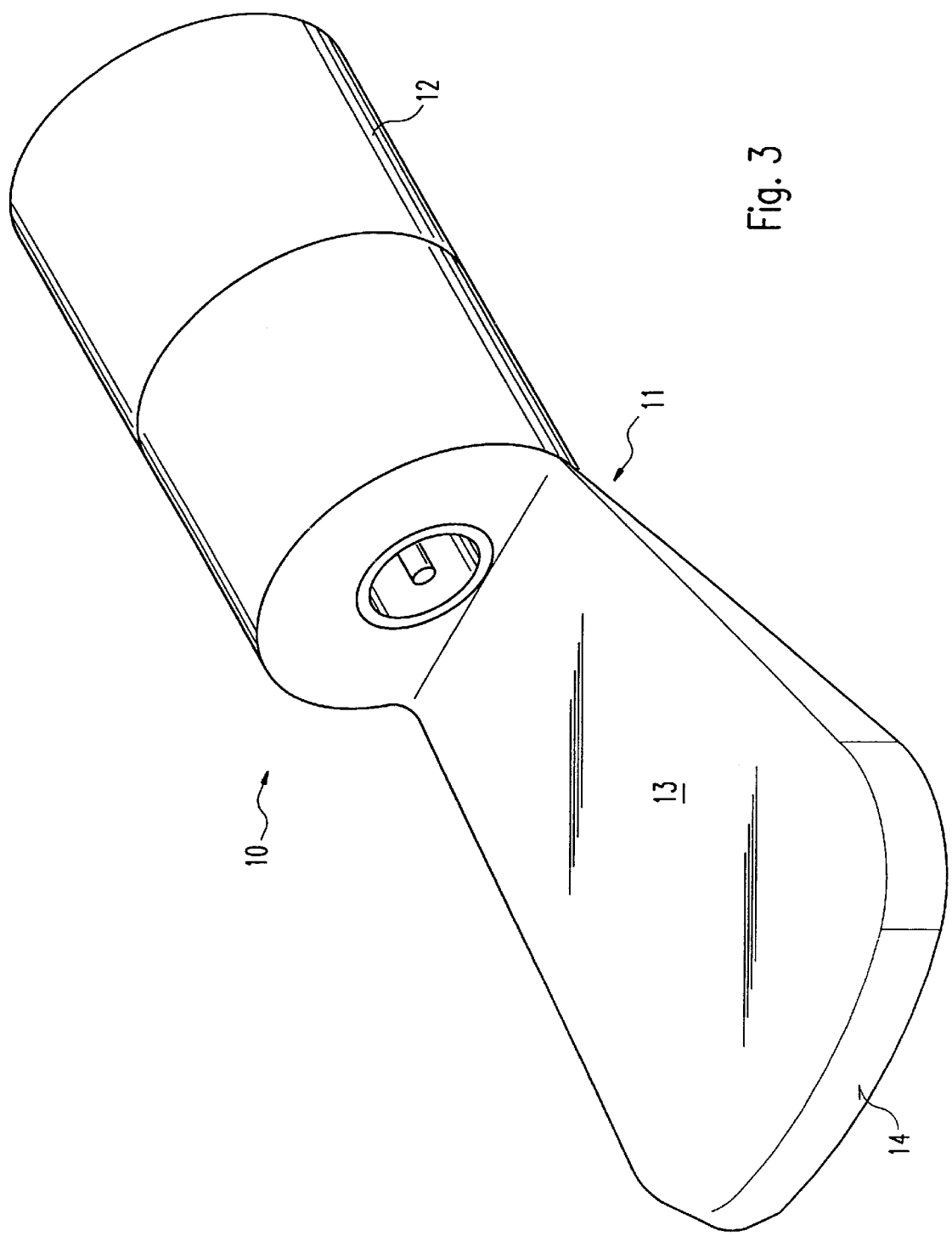

In the embodiment of the head 11 shown in FIG. 3, it has a spade shape and is intended to push tissue away.

The embodiment of the head 11 shown in FIG. 4 has a cutting edge 15 provided with teeth at the front boundary of the surface 13.

Figure 6:
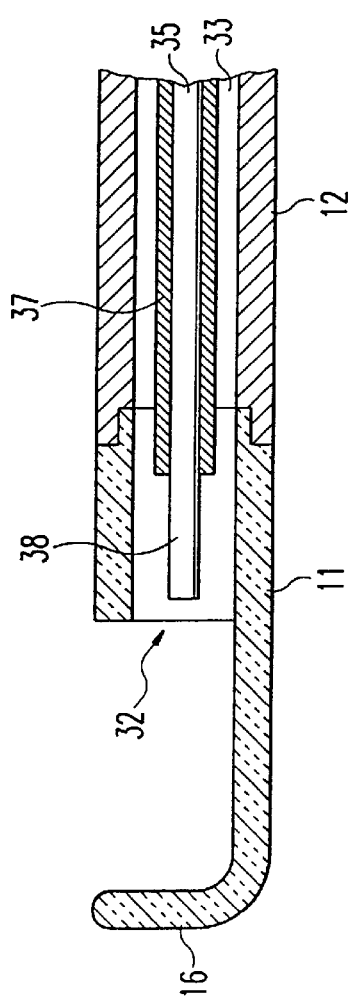
FIG. 6 shows a longitudinal section through an end region of the instrument according to FIG. 5.
Figure 5:
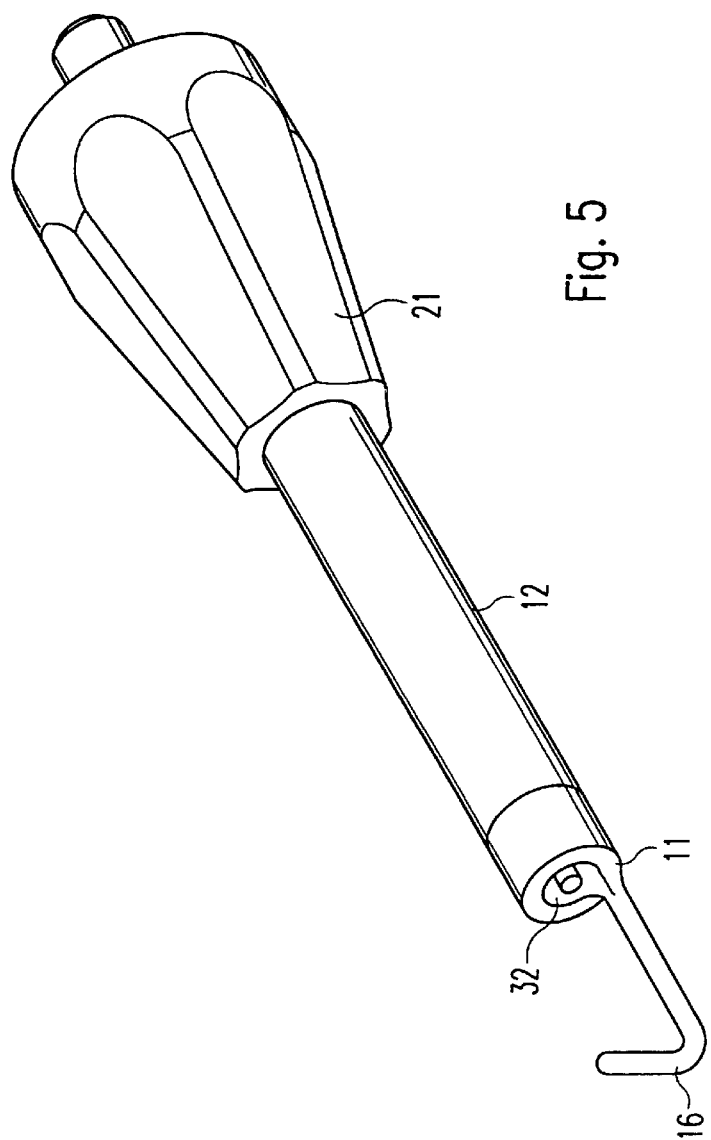
FIG. 5 is a perspective view of a hook-shaped working instrument.

In FIG. 5 a further embodiment of a head 11 is shown, which in this case comprises a hook 16. The hook 16, as can be seen in FIG. 6, is made integral with the head 11, and for this construction—as also in the exemplary embodiments shown previously and hereafter—electrically insulating and thermally stable ceramic materials are particularly suitable.

The head 11 is fixed in the shaft 12, which has a hollow interior and thus forms a gas conduit 33. In the shaft 12 or the gas conduit 33 an electrode holder is fixed, through the interior of which runs a wire to serve as current conductor 35, the (uninsulated) end of which projects from the electrode holder 37 to form the electrode 38. These elements are arranged in such a way that the electrode 38 is substantially concentric with the outlet 32 but—as can readily be seen in FIG. 6—is positioned somewhat behind the opening so that contact between the electrode 38 and the surrounding tissue is impossible.

The gas supply (through the gas conduit 33) is preferably adjusted so that a certain amount of gas flows continuously, even in the absence of a coagulation current. This measure prevents entry into the outlet 32 of liquid that might have some deleterious effect on the coagulation current.

Not only relatively simple dissection instruments like those shown in FIGS. 1 to 6 can be made out of electrically insulating (preferably ceramic) material; in fact, very much more complicated instruments can be so constructed, for instance a working instrument 10 with scissor blades 17, the cutting edges 15 of which are disposed very close to the coagulation device 30 or the outlet 32 with electrode 38 inside it. With such an arrangement, after a cut has been made, immediate coagulation of the opened tissue is possible.

In the further embodiment of the apparatus in accordance with the invention shown in FIG. 9, the working instrument 10 at its head 11 again comprises a cutting edge 15 in the vicinity of the coagulation device 30 with its gas outlet 32 containing an electrode 38. Here there are additionally provided two channels 51 and 52, which can be connected to sources of various kinds by appropriate conducting means. For example, one channel can be used as a suction channel, the other as a rinsing channel through which a liquid or a gas is provided, so that relatively large amounts of liquid can be sucked or (e.g., together with solid particles) washed away from the operation field. The crucial aspect of this embodiment of the invention is the fact that here, too, the accessory instruments, which in FIG. 9 take the form of channels, are disposed substantially in the immediate vicinity of the cutting edge 15 (or a corresponding hook, etc.). Because of this close proximity, during the process of cutting (opening of the tissue by means of a hook, spade etc.) or just after it the operator can carry out a second procedure, namely the above-mentioned coagulation or a rinsing, sucking or similar procedure, without changing instruments and substantially without displacing the instrument to an appreciable extent. As far as the actual construction of the working instrument 10 is concerned, the choice of material is of essential importance, because it must be ensured that the flow of coagulation current from the electrode 38 to the body tissue (not shown here) is preserved.

The working instruments described above, or the various heads of the working instruments, can be shaped according to the requirements of the operator, and even flexible working instruments such as loops can be produced with an appropriate choice of material. The instruments shown are not restricted to particular areas of application. They can be used both in open surgery and in endoscopic operations.

What is claimed is:

1. A dissection instrument for surgical operations, comprising:
   a non-conductive, mechanical working instrument including a non-conductive working end portion for the mechanical cutting, opening, pushing or pulling of tissue;
   a holding device mounted to the non-conductive, mechanical working instrument for moving the non-conductive, mechanical working instrument and locating the non-conductive working end portion in contact with tissue; and
   a coagulation device comprising,
   (a) a gas-supply conduit extending through the holding device to supply an ionizable gas to a region at the site of the non-conductive working end portion and the tissue; and
   (b) a current conductor to conduct a coagulation current, said current conduct or extending through the gas-supply conduit and including an electrode end adjacent the non-conductive working end portion, and an opposite end for coupling to an HF current source, to produce an electrical current conducted from the electrode end through plasma to the tissue for the purpose of coagulating, in particular stanching bleeding;
   wherein the non-conductive, mechanical working instrument is electrically insulated from the electrode end such that the coagulation current can be applied to the tissue without being conducted through the non-conductive, mechanical working instrument, even while the non-conductive working end portion is in contact with the tissue.

2. Dissection instrument according to claim 1, wherein the non-conductive, mechanical working instrument is made of a plastic, ceramic or other electrically insulating material.

3. Dissection instrument according to claim 1, wherein the non-conductive, mechanical working instrument is coated with a plastic, a ceramic material or other electrically insulating material.

4. Dissection instrument according to claim 1, wherein the electrode end includes an electrode holder and an electrode tip fixed close to the non-conductive working end portion.

5. Dissection instrument according to claim 1, wherein the gas-supply conduit includes a gas outlet which is disposed near the non-conducting working end portion at or surrounding the electrode end.

6. Dissection instrument according to claim 4, wherein the non-conductive, mechanical working instrument and the electrode holder are constructed substantially in one piece.

7. Dissection instrument according to claim 5, wherein the non-conductive, mechanical working instrument and the gas outlet are constructed substantially in one piece.

8. Dissection instrument according to claim 1, wherein the non-conductive, mechanical working instrument and the holding device are constructed substantially in one piece.

9. Dissection instrument according to claim 1, wherein the electrode end is constructed and disposed in such a way that a direct electrical contact between the electrode end and the tissue is prevented.

10. Dissection instrument according to claim 1, an including means for attaching an accessory instrument to the non-conductive, mechanical working instrument to provide for suction, rinsing or blowing or an additional electrosurgical instrument such as an electrode in the form of a needle, sphere, wire, loop or flat surface.

11. Dissection instrument according to claim 1, wherein the holding device is so constructed as to be exchangeable, with the simultaneous coupling and decoupling of the ionizable gas and HF current supplies.

12. Dissection instrument according to claim 1, wherein cleaning means are provided to keep the electrode end free of liquid or other soiling substances.

13. Dissection instrument according to claim 12, wherein the cleaning means comprise a separate gas conduit, which is so constructed that a stream of gas flows substantially continuously around the electrode end.

14. Dissection instrument according to claim 1, wherein the non-conductive working end portion comprises one of a cutting edge, a knife, scissors, a hook, a needle, and a loop.

* * * * *